(12) United States Patent
Douglas (10) Patent No.: US 10,413,707 B2
(45) Date of Patent: Sep. 17, 2019

(54) TRANSSEPTAL CROSSING GUIDEWIRE WITH FACETED PIERCING HEAD

(71) Applicant: Lake Region Manufacturing, Inc., Chaska, MN (US)

(72) Inventor: Jeanne Douglas, Shakopee, MN (US)

(73) Assignee: Lake Region Manufacturing, Inc., Chaska, MN (US)

( * ) Notice: Subject to any disclaimer, the term of this patent is extended or adjusted under 35 U.S.C. 154(b) by 0 days.

(21) Appl. No.: 15/695,117

(22) Filed: Sep. 5, 2017

(65) Prior Publication Data

US 2018/0064914 A1    Mar. 8, 2018

Related U.S. Application Data

(60) Provisional application No. 62/383,061, filed on Sep. 2, 2016.

(51) Int. Cl.
*A61M 25/09* (2006.01)
*A61B 17/22* (2006.01)
*A61B 17/34* (2006.01)
*A61B 17/00* (2006.01)

(52) U.S. Cl.
CPC ......... *A61M 25/09* (2013.01); *A61B 17/3478* (2013.01); *A61B 2017/00247* (2013.01); *A61B 2017/22044* (2013.01); *A61M 2025/09083* (2013.01); *A61M 2025/09175* (2013.01); *A61M 2025/09183* (2013.01); *A61M 2025/09191* (2013.01)

(58) Field of Classification Search
CPC ........ A61M 25/09; A61M 2025/09083; A61M 2025/09175; A61M 2025/09183; A61M 2025/09191; A61B 2017/00247; A61B 2017/22044; A61B 17/34; A61B 17/3417; A61B 10/0233
See application file for complete search history.

(56) References Cited

U.S. PATENT DOCUMENTS

| | | | |
|---|---|---|---|
| 5,685,820 A * | 11/1997 | Riek | A61B 1/00165 600/104 |
| 7,048,733 B2 | 5/2006 | Shah et al. | |
| 8,092,395 B2 * | 1/2012 | Lupton | A61M 25/09 600/585 |
| 8,882,697 B2 | 11/2014 | Sugimoto et al. | |
| 2010/0268029 A1 * | 10/2010 | Phan | A61B 1/00082 600/115 |

(Continued)

*Primary Examiner* — Devin B Henson
(74) *Attorney, Agent, or Firm* — Michael F. Scalise (57) ABSTRACT

A guidewire that is specifically designed for performing an intracardiac transseptal puncture procedure is described. A piercing head for the guidewire has a conically-shaped section that tapers to a cutting section comprised of three tapered facets extending to a pointed tip. The three facets form three cutting edges that each provide for smooth cutting of body tissue, for example, cutting of the septum wall. The cut tissue does not tend to close or relax as readily as if the tissue had been punctured with a conically-shaped piercing tip, for example, one that has a structure similar to a pencil tip, This helps with subsequently moving a catheter and similar medical device through the pierced body tissue. Consequently, the faceted piercing head leaves an opening having a diameter that is substantially similar to the maximum outer diameter of piercing head.

14 Claims, 8 Drawing Sheets

(56) References Cited

U.S. PATENT DOCUMENTS

| | | | |
|---|---|---|---|
| 2013/0324967 A1* | 12/2013 | Pillai | A61M 25/09 |
| | | | 604/506 |
| 2013/0345634 A1* | 12/2013 | Wach | A61M 25/0606 |
| | | | 604/164.01 |
| 2015/0173794 A1 | 6/2015 | Kurth et al. | |

* cited by examiner

TRANSSEPTAL CROSSING GUIDEWIRE WITH FACETED PIERCING HEAD

CROSS-REFERENCE TO RELATED APPLICATION

This application claims priority from U.S. provisional application Ser. No. 62/383,061, filed on Sep. 2, 2016.

BACKGROUND OF THE INVENTION

1. Field of the Invention

The present invention generally relates to a device for performing an intracardiac transseptal puncture procedure. More specifically, the present invention relates to a percutaneous device for making a transseptal puncture in the atrial septum of the heart. In particular, the present invention relates to devices and methods for puncturing the atrial septum vis the percutaneous route. That is for gaining access to the left atrium through the right atrium for diagnostic or therapeutic purposes.

2. Prior Art

Septal puncture through an intact atrial septum from the right atrium to the left atrium is often necessary. This is traditionally performed using rigid, long needles, such as Brockenbrough or Ross needles.

Figure 1:
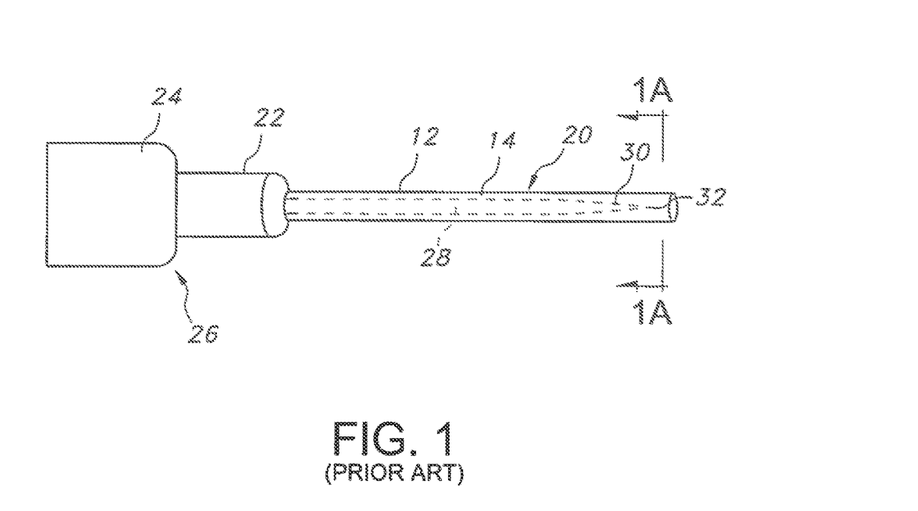
FIG. 1 is a plan view of a prior art transseptal puncture device 10 according to the prior art.

Another device that is specifically designed for the purpose of performing a septal puncture is illustrated in FIG. 1. This drawing is a plan view of the prior art transseptal puncture device 10 described in U.S. patent application Pub. No. 2015/0173794 to Kurth et al. This device is commercially available from Pressure Products Medical Supplies Inc. as the SafeSept® Transseptal Guidewire. The prior art transseptal puncture device includes a dilator 12 providing a lumen 14 axially disposed along a longitudinal axis. The dilator 12 has a blunt distal end 16 defining an opening 18 in open communication with the lumen 14. A guidewire 20 is axially disposed within the lumen of the dilator 12. A transcutaneous intravascular sheath 22 is also shown. The sheath 22 provides a conduit through which the transseptal puncture device 10 passes from outside the patient's body through a vessel, for example, the femoral vein, through the inferior vena cava to the right atrium. A control handle 24 is schematically depicted at the distal end 26 of the sheath 22.

As further shown in FIG. 1, the prior art guidewire 20 has a constant diameter through a major portion of its length. This constant diameter portion begins at the proximal end of the guidewire and is indicated by numerical designation 28. The constant diameter portion forms into a piercing head 30 having a conical taper extending to a distal pointed tip 32. The taper of the piercing head 30 is similar to the shape of a pencil head.

Figure 2:
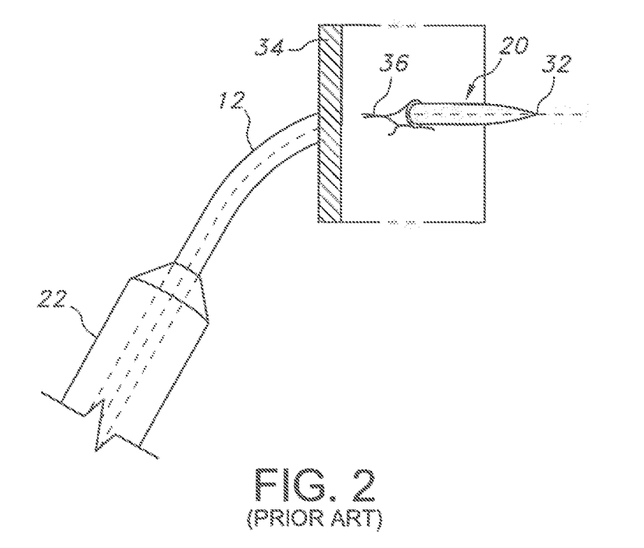
FIG. 2 is a schematic view showing the prior art transseptal puncture device 10 depicted in FIGS. 1 and 1A being used in an intracardiac transseptal puncture procedure.

A drawback of the prior art transseptal puncture device 10 is that when the guidewire 20 is used in an intracardiac transseptal puncture procedure, the conical-shaped taper of the piercing head 30 extending to the pointed tip 32 tends to puncture the septum wall 34 (FIG. 2) leaving the body tissue with a somewhat jagged cut, as indicated by numerical designation 36. Further, the tissue comprising the septum wall 34 is relatively pliable and supple, which means that the tissue readily relaxes back to its original shape. After the guidewire 20 is removed from the puncture site, the opening in the septum wall tends to close back to a diameter that is significantly less than the maximum diameter of the constant diameter portion 28 of the guidewire 20. This can make it difficult to move a catheter or other cardiac instrument through the pierced opening in the septum wall 34.

In that respect, while the prior art SafeSept® Transseptal Guidewire is suitable for use in performing an intracardiac transseptal puncture procedure, there is a need for an improved transseptal puncture device that when used to puncture the septum wall not only cuts the body tissue in a clean knife-like manner, but leaves an opening having a diameter that is substantially similar to the maximum diameter of the guidewire.

The transseptal puncture device of the present invention fulfills these needs.

SUMMARY OF THE OF INVENTION

The present invention relates to a guidewire that is specifically designed for performing an intracardiac transseptal puncture procedure. The guidewire has a piercing head comprising a conically-shaped section that tapers to a cutting section comprised of three tapered facets extending to a pointed tip. A cutting edge is formed where immediately adjacent facets meet. The three facets form three cutting edges that each provide for smooth cutting of body tissue, for example, cutting of the septum wall. Not only are the cuts less traumatic to body tissue, but the cut tissue does not tend to close or relax as readily as if the tissue had been punctured with a conically-shaped piercing tip, for example, one that has a structure similar to a pencil tip. This helps with subsequently moving a catheter and similar medical device through the pierced body tissue such as the pierced septum. Consequently, the faceted cutting head leaves an opening having a diameter that is substantially similar to the maximum diameter of the guidewire to which the cutting head is attached.

These and other aspects of the present invention will become more apparent to those of ordinary skill in the art by reference to the following description and the appended drawings.

BRIEF DESCRIPTION OF THE DRAWINGS

In the drawings, like reference numbers generally refer to the same parts throughout the different views. Also, the drawings are not necessarily to scale, emphasis instead generally being placed upon illustrating the principles of the present invention.

DETAILED DESCRIPTION OF THE INVENTION

Figure 3:
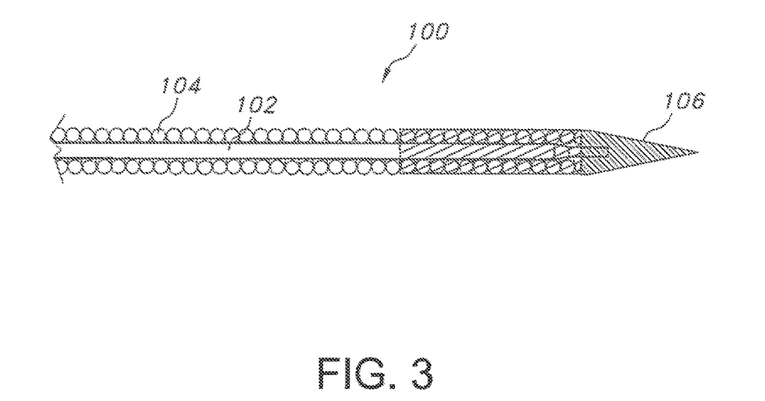
FIG. 3 is a side elevational view of the transseptal puncture guidewire 100 according to the present invention.
Figure 5:
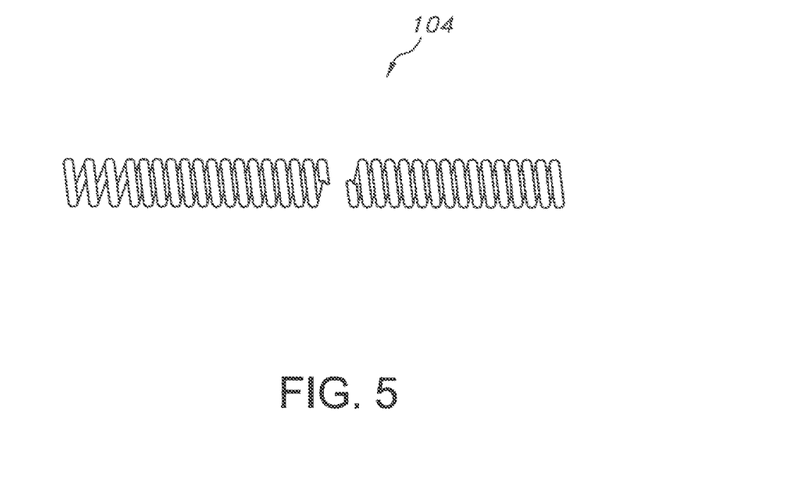
FIG. 5 is a side elevational view of the coil spring 104 for the transseptal puncture guidewire 100 shown in FIG. 3.
Figure 6:
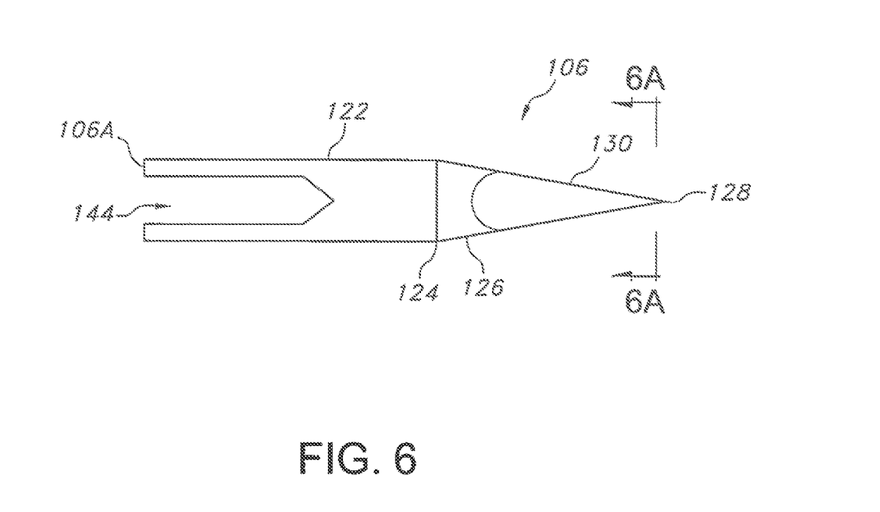
FIG. 6 is a side elevational view of a piercing head 106 for the transseptal puncture device 100 shown in FIG. 3.
Figure 6A:
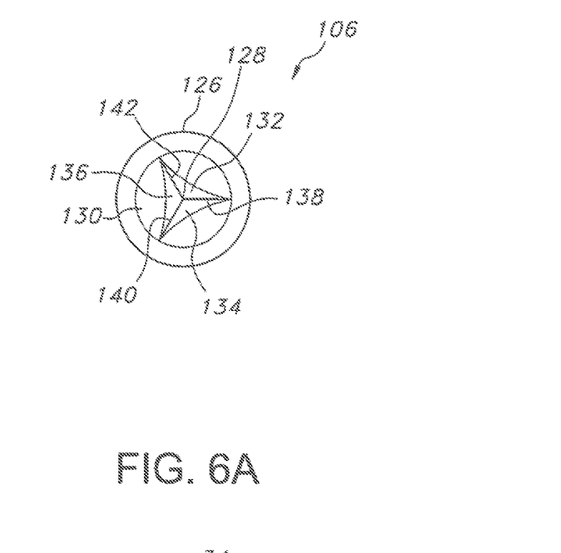
FIG. 6A is a cross-sectional view taken along line 6A-6A of FIG. 6.
Figure 7:
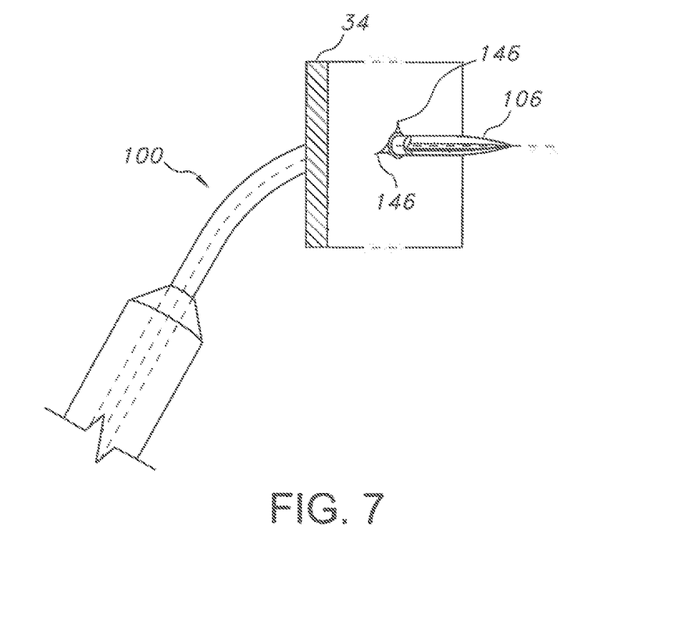
FIG. 7 is a schematic view showing the transseptal puncture device 100 of the present invention being used in an intracardiac transseptal puncture procedure.

FIGS. 3 and 7 illustrate a transseptal puncture guidewire 100 according to the present invention. The guidewire 100 is generally comprised of an elongated metal core wire 102 (FIG. 4) supporting a coil spring 104 (FIG. 5). The core wire 102 is connected to a piercing head 106 (FIGS. 6 and 6A). The core wire 102, for example, of stainless steel, extends along s longitudinal axis A-A from a proximal end 102A to a distal end 102B. The distal end 102B of the core wire 102 is connected to the piercing head 106. In use, the piercing head 106 forms the leading end of the guidewire 100 as it is urged through body tissue, for example, through the septum.

Figure 4:
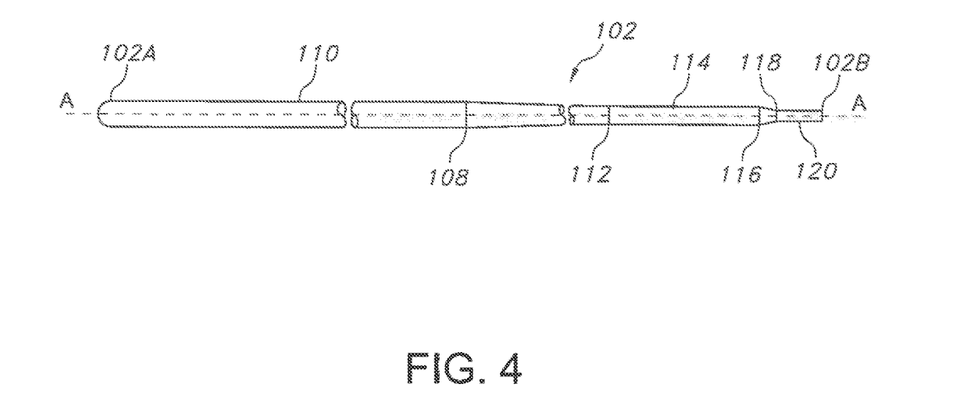
FIG. 4 is a plan view of a core wire 102 for the transseptal puncture guidewire 100 shown in FIG. 3.

As particularly shown in FIG. 4, over most of its length from the proximal end 102A to a location indicated at 108, the core wire 102 is of a first portion 110 of a first circular transverse cross-section of a constant diameter in the range of 0.2 mm to 0.5 mm. At location 108, the core wire 102 tapers downwardly and distally towards location 112 where a second circular transverse cross-section portion 114 of a second constant diameter begins. The second portion 114 extends to location 116. At location 116, the core wire 102 again tapers downwardly and distally towards location 118 where there is a third circular transverse cross-section portion 120 of a third constant diameter. The third portion 120 extends to the distal end 102B. The core wire 102 is shown tapering in two steps, however, in alternate embodiments, it may have a uniform diameter throughout its length, or taper in one or more than two steps. Tapers are preferred as they help increase the flexibility of the core wire 102 and the assembled guidewire 100.

The tightly wound helical coil spring 104 of metal, for example, of stainless steel, serves as a sleeve that preferably extends from the first tapered portion beginning at location 108 to the distal end 102B of the core wire 102. The coil spring 104 is of a generally circular transverse cross-section of substantially constant outer diameter in the range of 0.2 mm to 0.5 mm.

FIGS. 6 and 6A illustrate the piercing head 106 which is comprised of a shank 122 of a constant circular transverse cross-section extending from a proximal end 106A to location 124. At location 124, the piercing head 106 forms into a conically-shaped section 126 that tapering downwardly and distally toward a longitudinal axis of the head. However, as clearly illustrated in FIG. 6A, the conical section 126 does not extend all the way to the distal pointed tip 128. Instead, the conical section 126 forms into a cutting section 130 comprised of three tapered facets 132, 134 and 136, each facet being a generally planar surface that extends downwardly and distally to the pointed tip 128.

FIG. 3 shows that the distal end of the coil spring 104 is secured to the proximal end 106A of the piercing head 106. In this position, a first outer diameter of the distal end of the coil spring 014 is similar to a second outer diameter of the proximal end 106A of the piercing head 106.

A novel aspect of the present invention is that immediately adjacent or adjoining facets form a cutting edge that provides for smooth cutting of body tissue, for example, cutting of the septum wall 34. In particular, a first cutting edge 138 is formed at the junction of facets 132 and 134, a second cutting edge 140 is formed at the junction of facets 134 and 136, and a third cutting edge 142 is formed at the junction of facets 136 and 132.

While three facets 132, 134 and 136 are shown, a piercing head with a plurality of facets and intermediate cutting edges is contemplated by the scope of the present invention. In that light, the piercing head can have four, five, six or more facets with a like number of intermediate cutting edges.

As shown in FIG. 6, the shank 122 of piercing head 106 includes a blind bore 144. Bore 144 begins at a proximal end 106A of the head 106 and extends axially part-way along the shaft length. The blind bore 144 is sized and shaped to receive the third portion 120 of the core wire 102 having the third circular transverse cross-section. The third portion 120 of the core wire 102 is secured in the blind bore 144 by any one of a number of methods known to those skilled in the art including adhesive, laser welding, and the like.

Figure 1A:
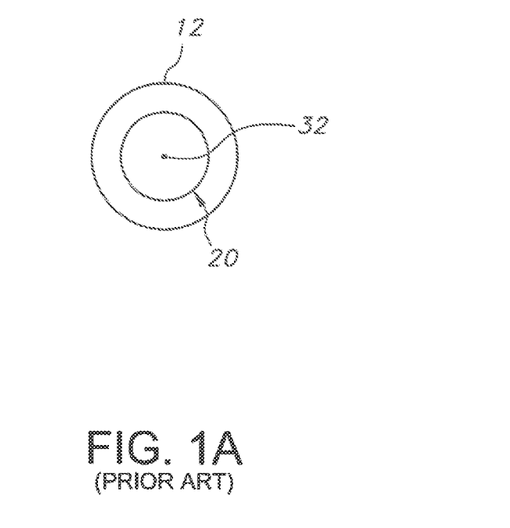
FIG. 1A is a cross-sectional view taken along line 1A-1A of FIG. 1.

FIG. 7 illustrates an exemplary puncture of the septum wall 34. This drawing shows that the cutting edges 138, 140 and 142 are specifically designed to cut through body tissue in a clean and relatively less traumatic manner than the prior art conical-shaped piercing head 30 having the pointed tip 32. Upon piercing body tissue and after having been completely moved through the tissue, the cutting edges 138, 140 and 142 produce cleanly severed cuts 146. Not only are the cuts 146 less traumatic to body tissue than the puncture that is produced with the prior art device 10 illustrated in FIGS. 1, 1A and 2, but the cut tissue does not tend to close or relax as readily, which helps with subsequently moving a catheter and similar medical device through the punctured tissue, for example through the septum 34 and into the left atrium. In that respect, the present piercing head 106 leaves an opening having a diameter that is substantially similar to the maximum diameter of the shank 122 of the piercing head.

Figure 8A:
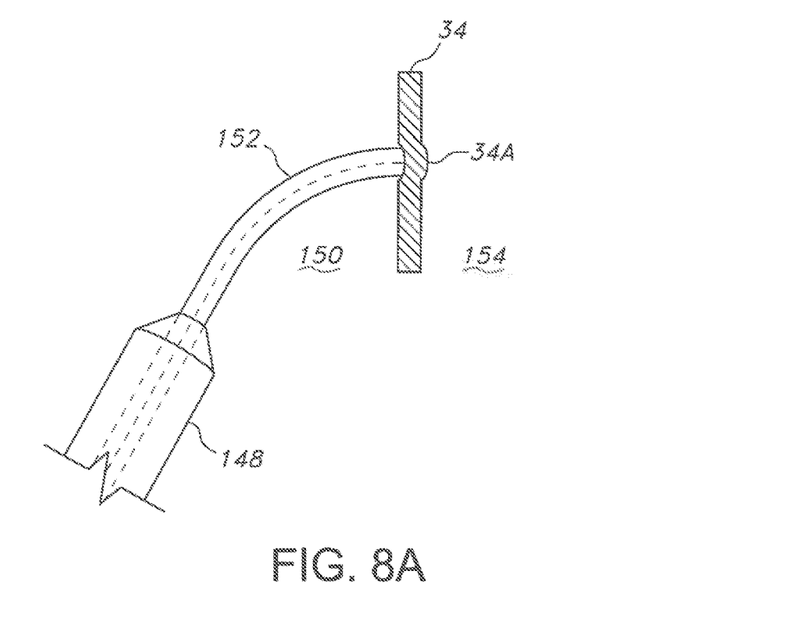
FIGS. 8A to 8E depict the steps in an illustrative method for puncturing an atrial septum with the transseptal puncture guidewire 100 of the present invention.

FIGS. 8A to 8E depict the steps of an illustrative method for puncturing an atrial septum with the transseptal puncture guidewire 100 of the present invention. Referring to FIG. 8A, the illustrative method includes the step of introducing an intravascular sheath 148 into a vessel to access the lumen of the right atrium 150. The sheath 148 may have a distal taper to enhance its advancement. After the sheath 148 is properly positioned in the right atrium 150, a blunt dilator 152 is advanced distally toward the atrial septum 34 and positioned against septum primum 34A at the puncture site. The blunt dilator 152 is then pushed against septum primum 34A until some tenting of the atrial septum 34 is visible. The tenting should be sufficient to correctly identify the puncture site in the septum primum 34A. Alternatively, visualization techniques such as, three-dimensional echocardiogram, ultrasound, or magnetic resonance imaging can be used without tenting. Moreover, some amount of tenting also assists with the puncture itself.

Figure 8B:
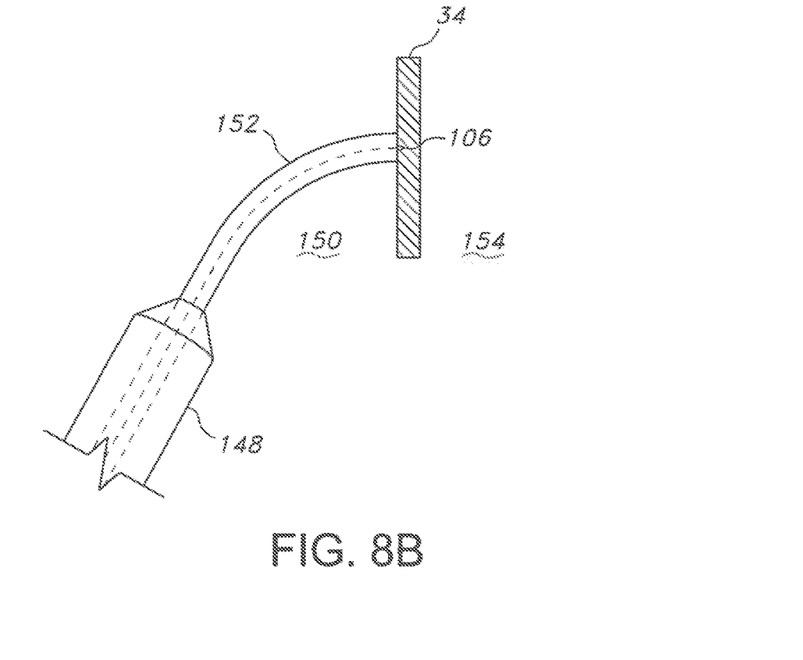

Referring to FIG. 8B, once the dilator 152 is positioned against the septum primum 34A, the guidewire 100 is advanced relative to the dilator 152 through the septum 34. At least about 10 mm up to about 30 mm of the guidewire 100 should extend from the distal end of the dilator 152. In one embodiment, movement of the guidewire 100 is by manual manipulation. Alternatively, movement of the guidewire 100 may be automated.

Figure 8C:
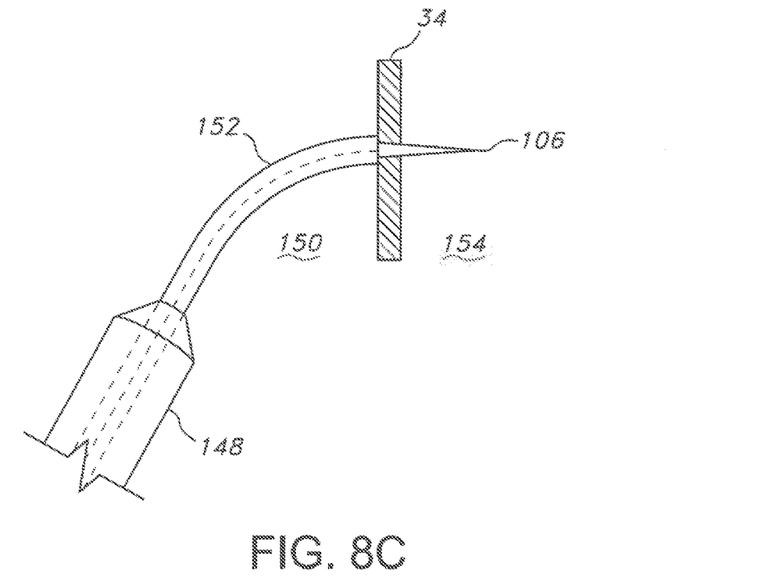

Referring now to FIG. 8C, once the distal end of the guidewire 100 is positioned within the septum 34 the piercing head 106 is moved into the left atrium 154. As previously discussed, this movement produces clearly severed cuts 146 (FIG. 7) leaving an opening having a diameter that is substantially similar to the maximum diameter of the shank 122 of the piercing head 106. The guidewire 100 may be advanced approximately 10 cm to sufficiently see the guidewire and its piercing head 106 outside of the cardiac silhouette. Typically, visualization of the guidewire 100 within the pulmonary veins is done using x-ray imaging or other imaging techniques.

Figure 8D:
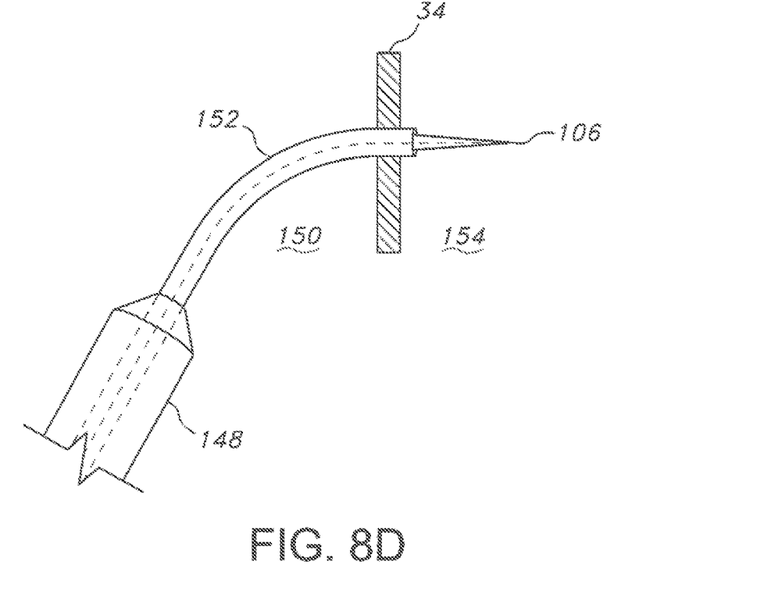

FIG. 8D shows the dilator 152 being advanced through the opening cut into the septum and positioned in the left atrium 34.

Figure 8E:
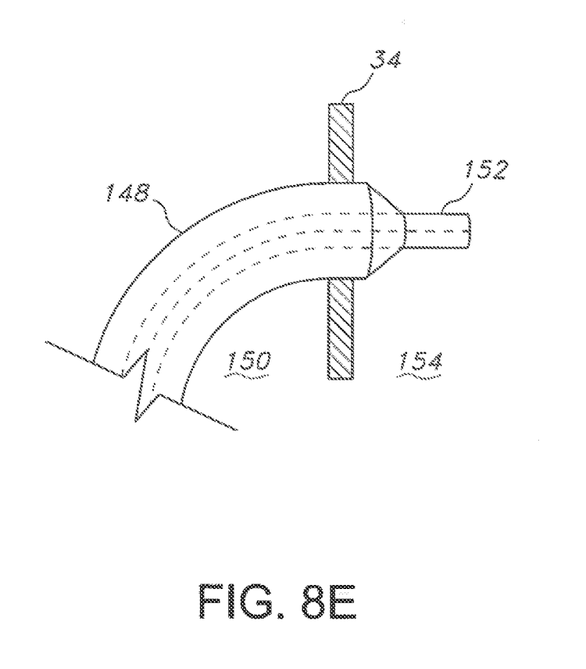

Referring to FIG. 8E, standard catheterization laboratory procedures are utilized to place the sheath 148 within the left atrium 154. Once the sheath 148 is in the left atrium 154, the other components of the device, for example, the guidewire 100 and the dilator 152, can be completely removed from the sheath 148 and the sheath can be used to deliver implants, for example, an atrial occluder for the treatment of a patent foramen ovale, sutures, or other intracardiac therapeutic devices.

It is appreciated that various modifications to the present inventive concepts described herein may be apparent to those of ordinary skill in the art without departing from the scope of the present invention as defined by the herein appended claims.

What is claimed is:

1. A guidewire, comprising:
    a) a core wire extending along a longitudinal axis to a core wire proximal end and to a core wire distal end, wherein the core wire comprises at least one tapered section that tapers from a first diameter to a second, lesser diameter at the core wire distal end;
    b) a piercing head extending distally from the core wire distal end, wherein the piercing head has three facets, each facet extending distally and downwardly to converge at a distal pointed tip that is coincident with the longitudinal axis, and wherein a cutting edge resides where adjacent ones of the facets are coincident to thereby provide the piercing head with three cutting edges, each of the cutting edges extending to the distal pointed tip at the longitudinal axis; and
    c) a helically wound coil spring comprising a bore extending to a coil spring proximal end and to a coil spring distal end,
    d) wherein the core wire extends through the bore of the coil spring.

2. The guidewire of claim 1, wherein at least one of the core wire and the coil spring is comprised of stainless steel.

3. The guidewire of claim 1, wherein the distal end of the coil spring is secured to a proximal end of the piercing head.

4. The guidewire of claim 1, wherein a first outer diameter of the distal end of the coil spring is similar to a second outer diameter of the proximal end of the piercing head.

5. The guidewire of claim 1, wherein the first diameter of the core wire resides at the core wire proximal end.

6. The guidewire of claim 1, wherein the piercing head has a conical section located intermediate a proximal section having a constant circular transverse cross-section and the distal three facets.

7. The guidewire of claim 6, wherein the core wire tapers from the first diameter ranging from 0.2 mm to 0.5 mm to the second, lesser diameter at the core wire distal end.

8. The guidewire of claim 1, wherein the core wire extends through the bore of the coil spring with an inner surface of the coil spring contacting an outer surface of the core wire along the coil spring length extending to the coil spring proximal and distal ends.

9. A guidewire, comprising:
    a) a core wire having a uniform cross-sectional diameter extending along a longitudinal axis to a core wire proximal end and to a core wire distal end;
    b) a piercing head extending distally from the core wire distal end, wherein the piercing head has three facets, each facet extending distally and downwardly to converge at a distal pointed tip that is coincident with the longitudinal axis, and wherein a cutting edge resides where adjacent ones of the facets are coincident to thereby provide the piercing head with three cutting edges, each of the cutting edges extending to the distal pointed tip at the longitudinal axis; and
    c) a helically wound coil spring having a bore extending along a coil spring length to a coil spring proximal end and to a coil spring distal end,
    d) wherein the core wire extends through the bore of the coil spring with an inner surface of the coil spring contacting an outer surface of the core wire along the coil spring length to the coil spring proximal and distal ends, and
    e) wherein the distal end of the coil spring is secured to a proximal end of the piercing head with a first outer diameter of the distal end of the coil spring being similar to a second outer diameter of the proximal end of the piercing head.

10. The guidewire of claim 9, wherein at least one of the core wire and the coil spring is comprised of stainless steel.

11. The guidewire of claim 9, wherein the piercing head has a conical section located intermediate a proximal section having a constant circular transverse cross-section and the distal three facets.

12. A guidewire, comprising:
    a) a core wire extending along a longitudinal axis to a proximal core wire end and to a distal core wire end, wherein the core wire comprises at least one tapered section intermediate a proximal constant-diameter section of a greater diameter than a distal constant-diameter section of a lesser diameter;
    b) a distal piercing head connected to the distal constant diameter section of the core wire, wherein a distal section of the piercing head consists of three facets, each facet extending distally and downwardly to converge at a distal pointed tip that is coincident with the longitudinal axis; and
    c) a helically wound coil spring having a bore extending along a coil spring length to a coil spring proximal end and to a coil spring distal end, wherein the core wire extends through the bore of the coil spring with an inner surface of the coil spring contacting an outer surface of the core wire along the coil spring length to the coil spring proximal and distal ends, and
    d) wherein the distal end of the coil spring is secured to a proximal end of the piercing head with the coil spring distal end residing at least at one of the at least one tapered section and the distal constant diameter section of the core wire.

13. The guidewire of claim 12, wherein at least one of the core wire and the coil spring is comprised of stainless steel.

14. The guidewire of claim 12, wherein the piercing head comprises a conical section located intermediate a proximal section having a constant circular transverse cross-section and the distal section consisting of the three facets.

* * * * *